United States Patent
Basini et al.

(10) Patent No.: US 11,492,315 B2
(45) Date of Patent: Nov. 8, 2022

(54) PROCESS FOR THE PRODUCTION OF METHANOL FROM GASEOUS HYDROCARBONS

(71) Applicant: ENI S.P.A., Rome (IT)

(72) Inventors: Luca Eugenio Riccardo Basini, San Donato Milanese (IT); Chiara Busto, Novara (IT); Michele Villani, San Donato Milanese (IT)

(73) Assignee: ENI S.P.A., Rome (IT)

( * ) Notice: Subject to any disclaimer, the term of this patent is extended or adjusted under 35 U.S.C. 154(b) by 0 days.

(21) Appl. No.: 17/277,516

(22) PCT Filed: Sep. 18, 2019

(86) PCT No.: PCT/IB2019/057842
§ 371 (c)(1),
(2) Date: Mar. 18, 2021

(87) PCT Pub. No.: WO2020/058859
PCT Pub. Date: Mar. 26, 2020

(65) Prior Publication Data
US 2021/0347716 A1    Nov. 11, 2021

(30) Foreign Application Priority Data
Sep. 19, 2018    (IT) .................. 102018000008721

(51) Int. Cl.
*C07C 29/151*    (2006.01)
*C25B 1/04*    (2021.01)

(52) U.S. Cl.
CPC ............ *C07C 29/1518* (2013.01); *C25B 1/04* (2013.01)

(58) Field of Classification Search
CPC ....... C07C 29/00; C07C 29/1518; C01B 3/48; C01B 3/30; C01B 3/26; C01B 2203/141;
(Continued)

(56) References Cited

U.S. PATENT DOCUMENTS

| 2015/0087865 A1* | 3/2015 | Iaquaniello ............... C01B 3/30 252/373 |
| 2020/0207632 A1* | 7/2020 | Han ........................ C01B 3/382 |
| 2021/0061655 A1* | 3/2021 | El-Halwagi ............... C01B 3/50 |

FOREIGN PATENT DOCUMENTS

| WO | 2016016251 A1 | 2/2016 |
| WO | 2017190224 A1 | 11/2017 |

OTHER PUBLICATIONS

International Search Report dated Dec. 18, 2018 for PCT application No. PCT/IB2019/057842.
(Continued)

*Primary Examiner* — Jafar F Parsa
(74) *Attorney, Agent, or Firm* — Ruggiero McAllister & McMahon LLC

(57) ABSTRACT

There is a process for the production of methanol from gaseous hydrocarbons. The process has the following stages: (a) treating said gaseous hydrocarbons in a desulfurization unit to produce a desulfurized hydrocarbon gas; (b) reacting the desulfurized gas with an oxidizing flow by means of a short contact time partial catalytic oxidation reaction to produce synthesis gas; (c) producing hydrogen by electrolysis of water; (d) mixing and compressing synthesis gas and hydrogen; and (e) sending said compressed mixture to a methanol synthesis unit to produce methanol.

13 Claims, 4 Drawing Sheets

(58) Field of Classification Search
CPC ...... C01B 2203/043; C01B 2203/1235; C01B 2203/0283; C01B 2203/261; C01B 2203/0233
See application file for complete search history.

(56) References Cited

OTHER PUBLICATIONS

Written Opinion dated Dec. 18, 2018 for PCT application No. PCT/IB2019/057842.

* cited by examiner

PROCESS FOR THE PRODUCTION OF METHANOL FROM GASEOUS HYDROCARBONS

CROSS-REFERENCE TO RELATED APPLICATIONS

The present application claims priority from PCT Application No. PCT/I132019/057842, filed Sep. 18, 2019, which claims priority from Italy Patent Application No. 102018000008721, filed Sep. 19, 2018, both of which are incorporated herein by reference in their entireties.

FIELD OF THE DISCLOSURE

The present disclosure relates to a process for the production of methanol from gaseous hydrocarbons, such as natural gas, associated petroleum gas, fuel-gas produced in a refinery or in certain chemical plants, or biogas.

SUMMARY OF THE DISCLOSURE

The main object of the process to which this patent application relates is to produce methanol by reducing or eliminating $CO_2$ emissions into the atmosphere, and to convert the $CO_2$ present in the gaseous hydrocarbons feed into methanol. The process described and claimed is particularly suitable for industrial applications treating hydrocarbon gases rich in $CO_2$ where a conventional $CO_2$ separation and sequestration process is not possible nor advantageous.

There is a process for the production of methanol from gaseous hydrocarbons, comprising the following stages:
a) treating said gaseous hydrocarbons in a desulfurization unit to produce a desulfurized hydrocarbon gas;
b) reacting the desulfurized gas with an oxidizing flow by means of a short contact time partial catalytic oxidation reaction to produce synthesis gas;
c) producing hydrogen by electrolysis of water;
d) mixing and compressing synthesis gas and hydrogen; and
e) sending said compressed mixture to a methanol synthesis unit to produce methanol.

DETAILED DESCRIPTION OF THE DISCLOSURE

Figure 1:
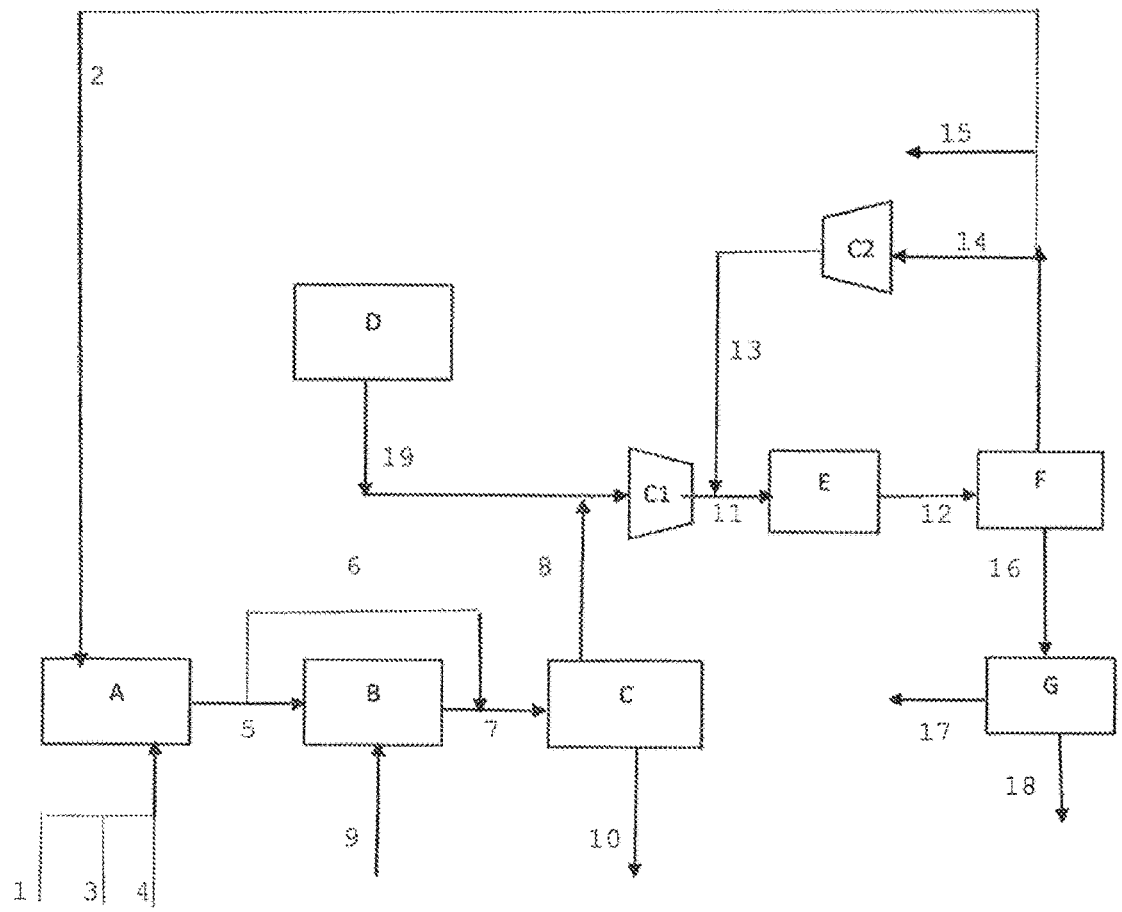
FIG. 1 depicts an embodiment of a process for production of methanol according to the present disclosure.

In the present patent application all the operating conditions included in the text are to be considered to be preferred conditions, even if not so expressly stated.

For the purposes of this description the terms "to comprise" or "to include" also include the terms "to consist of" or "to consist essentially of".

For the purposes of this description, definitions of ranges always include the end members unless otherwise specified.

Methanol ($CH_3OH$) is a colorless flammable liquid and at ambient temperature and pressure contains less oxygen and more hydrogen than any other liquid oxygenated fuel having a single carbon atom. It is the chemical commodity most widely produced and used. Its consumption in 2017 amounted to about 65 MTPA (Million Tons per Year) and production capacity exceeds 70 MTPA (IHS Chemical 2014, Methanol Report). About 90% is used in the chemical industry and the remaining 10% in the production of energy. Methanol may also be used as a fuel in internal combustion engines mixed with other hydrocarbons, and this possibility, so far little exploited, has great potential. Methanol synthesis reactions are highly exothermic and typically take place at temperatures between 250° C. and 350° C. and pressures of between 50 ATM and 100 ATM. Thermodynamic equilibrium limits conversion per pass and plants include a recycling loop to increase it. The main reactions occurring in methanol synthesis reactors can be represented by equations [1-3].

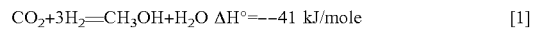

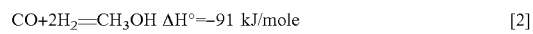

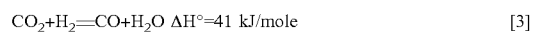

As may be seen, $CO_2$ is a reagent in methanol synthesis processes, but for the process to take place with high yields the synthesis gas composition must maintain the M=($H_2$—$CO_2$)/($CO_2$+CO) ratio ([4]), at values close to 2 v/v in order to avoid low conversions per pass and high volumes of purge gas in the recycling loop. In addition, a high $CO/CO_2$ ratio is also required to minimize the formation of by-products (e.g. $CH_4$).

There are many process schemes for the production of methanol that integrate synthesis gas production, Water Gas Shift, methanol synthesis, Pressure Swing Adsorption and product separation and purification sections.

The thesis "Methanol Production via Short Contact Time-Catalytic Partial Oxidation" (Faculty of Civil and Industrial Engineering; Master's Degree Course in Chemical Engineering, Rome, Federica Scirè; 1420915, A/A 2014/2015) describes the process scheme indicated in FIG. 4 typically used for large capacity plants using natural gas as hydrocarbon feedstock (5000 MTPG of methanol; CHEMSYSTEM PERP PROGRAM Methanol: 2012-5; 2013; A. Yang, Y. L. Song).

This process provides for:
1. the production of $O_2$ (500) by means of an air separation unit (ASU);
2. de-sulfurisation and removal of $CO_2$ from natural gas (100, SEPDES);
3. condensation and stabilisation of liquid hydrocarbons (300, STAB)
4. preheating the hydrocarbon feedstock to about 550-600° C. (SYNGEN);
5. a pre-reforming process (SYNGEN);
6. the production of synthesis gas with an AutoThermal Reforming Reactor (ATR, SYNGEN) according to reactions [5-7]:

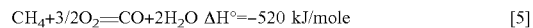

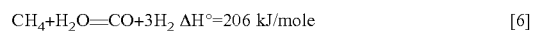

It also provides for adjustment of the composition of the synthesis gas to reach a value of M of about 2 v/v, through a $CO_2$ removal unit or a Pressure Swing Adsorption (PSA) unit. This last separates a stream of pure $H_2$ (800) from an aliquot of the recycled gas from the methanol synthesis loop, which is re-inserted into the synthesis gas, and a stream of purge gas containing mainly CO and $CO_2$ (900) which is burnt to produce energy. The synthesis gas with an M of about 2 v/v is compressed from a pressure typically near to 30 ATM to values between 60-100 ATM which are useful for the synthesis of methanol. Methanol (MeOH) synthesis takes place according to reactions [1-3]. The condensate is separated and the unconverted synthesis gas is recycled. The diagram in FIG. 4 includes a produced methanol purification block (PUR) and a produced methanol storage block (STOR).

This scheme provides three points where $CO_2$ is emitted:
(a) in the unit removing $CO_2$ from raw natural gas or other hydrocarbon sources that may be used (e.g. associated petroleum gas, fuel gas produced in refinery circuits or from other chemical plants, biogas);
(b) in the furnaces for preheating reagents fed to the synthesis gas production section; and
(c) in the section adjusting the composition of the synthesis gas to achieve values of M=2 v/v in the methanol synthesis feed.

If it is then considered that the ASU unit for the generation of oxygen consumes electricity, the calculation of the $CO_2$ emitted per unit of methanol produced must also consider the emissions associated to this unit operation.

$CO_2$ emissions are even higher in plants that use Steam Reforming (SR) for producing synthesis gas, because in this case, the emissions from the reforming furnace required to provide heat for the strongly endothermic Steam Reforming reactions are even higher, as can be seen from reactions [8-9].

$$CH_4 + H_2O = CO + 3H_2 \quad \Delta H° = 206 \text{ kJ/mole} \quad [8]$$

$$CH_4 + CO_2 = CO + 2H_2 \quad \Delta H° = 247 \text{ kJ/mole} \quad [9]$$

$$CH_4 + 1/2 O_2 = CO + H_2 \quad \Delta H° = -38 \text{ kJ/mole} \quad [10]$$

The thesis "Methanol Production via Short Contact Time-Catalytic Partial Oxidation" (Faculty of Civil and Industrial Engineering; Master's Degree Course in Chemical Engineering, Rome, Federica Scirè; 1420915, A/A 2014/2015) also describes the process scheme shown in FIG. 3.

The document also quantifies emission reductions in processes using SCT-CPO technology in the production of methanol and a natural gas feed containing from 0.5 to 30.0% v/v of $CO_2$.

If the possibilities offered by the SCT-CPO technology are combined with the possibilities offered by water electrolysis systems, process solutions are obtained that make possible, first of all, to avoid huge quantities of $CO_2$ emissions and that also consume the one contained in natural gas or in general in any hydrocarbon gas feed containing $CO_2$, such as bio-gas, associated petroleum gas, some refinery gases, and some industrial process purge gases.

These solutions can therefore replace or supplement those currently used in gas fields with a high $CO_2$ content, such as the amine washing and re-injection into fields that are still able to contain it, or into fields where re-injection allows Enhanced Oil Recovery (EOR) operations.

Figure 3:
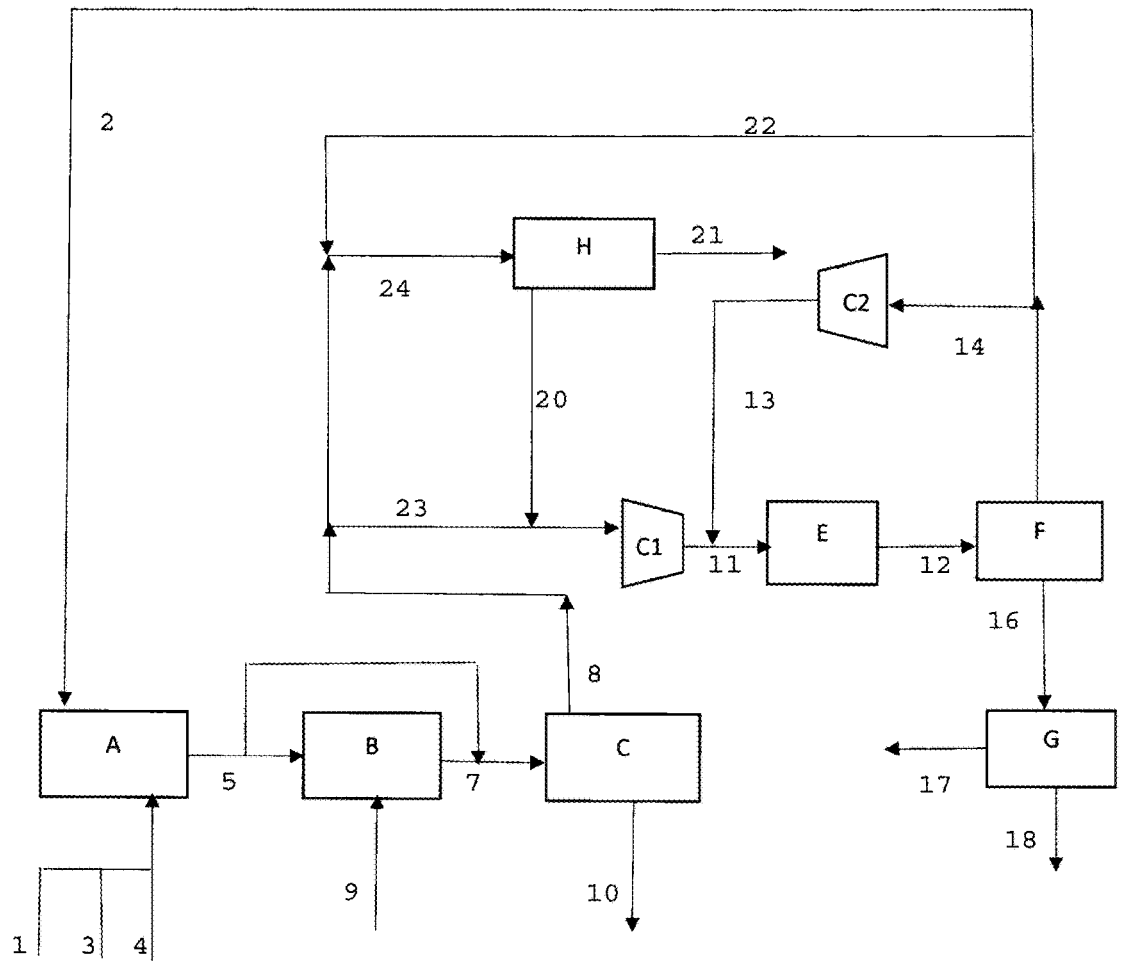
FIG. 3 depicts a process for the production of methanol according to the prior art.

It is important to notice at this point that one of the $CO_2$ emission points in methanol synthesis processes can be avoided by using proprietary SCT-CPO technology, which does not require pre-heating furnaces for the reagent feed nor even pre-reforming units of the gaseous hydrocarbon feedstock (FIG. 3). The chemistry underlying SCT-CPO processes has been described in many documents in the literature and is essentially based on the two main equations [10] and [7].

Integrated processes using short contact time catalytic partial oxidation technology have been described in patent applications WO 2016/016251, WO 2016/016253, WO 2016/016256 and WO 2016/016257.

In order to overcome the drawbacks and limitations of the known art, the Applicant has found a process for producing methanol from gaseous hydrocarbons, such as natural gas, associated petroleum gas from oil fields, fuel-gas produced in refineries and some chemical plants, and bio-gas. This process integrates the production of synthesis gas, the electrolysis of water and the synthesis of methanol to avoid $CO_2$ emissions and to consume the $CO_2$ present in the gaseous hydrocarbons.

The object of the present patent application is therefore a process for producing methanol from gaseous hydrocarbons which includes the following stages:
f) treating the said gaseous hydrocarbons in a desulfurization unit to produce a desulfurized hydrocarbon gas;
g) reacting the said desulfurized gas with an oxidizing flow by means of a short contact time catalytic partial oxidation reaction to produce synthesis gas;
h) producing hydrogen by electrolysis of water;
i) mixing and compressing the synthesis gas and hydrogen; and
j) sending the said compressed mixture to a methanol synthesis unit to produce methanol.

Advantageously, through the process described and claimed, it is possible to integrate or completely replace the production of $H_2$ obtained from a Pressure Swing Adsorption (PSA) unit, as typically included in the methanol synthesis schemes known in the state of the art. The PSA unit has the function of separating a high pressure flow of pure $H_2$ from purge flow rich in $CO_2$ and CO that is removed and typically burned, while the hydrogen is re-injected into the methanol synthesis recycling.

$H_2$ is mixed with the synthesis gas to correct the feed composition to obtain a $(H_2-CO_2)/(CO+CO_2)$ ratio close to 2 (v/v).

Since the PSA produces a high pressure flow of $H_2$ and a low-pressure purge containing $CO_2$ and CO, which are typically burned, its partial or total replacement by a water electrolysis system for the production of $H_2$ makes it possible to avoid the associated $CO_2$ emissions.

By exploiting the technology of short contact time partial catalytic oxidation (SCT-CPO), in particular the SCT-CPO technology owned by Eni S.p.A., it is possible to avoid the use of furnaces for preheating the feed, that would produce $CO_2$, by using instead gas-gas exchangers utilizing the waste heat from the process here described and claimed.

A further advantage is the possibility of dimensioning the water electrolysis unit in order to render available not only the hydrogen but also the oxygen necessary for the synthesis gas production process, thus replacing both the PSA units and the air separation units (ASU).

If the gaseous hydrocarbons contain significant quantities of $CO_2$, for example more than 5% in volume, the process described and claimed, enables the conversion of the carbon dioxide into methanol, consuming it.

The electrical energy required for the electrolysis reaction can be obtained from different sources and in particular:

i) by expanding the process steam export inside a steam turbine,
ii) from renewable sources.

The entire process described and claimed therefore enables greenhouse gas emissions (Greenhouse Gases or GHG), and in particular carbon dioxide, to be eliminated or significantly reduced, making it sustainable.

Moreover, if the process described and claimed, makes use of gaseous hydrocarbons with high $CO_2$ content, such as bio-gas, it is possible to produce methanol which can be considered to be an "advanced fuel" for use in internal combustion engines.

The process solution here described also makes it possible a relevant increase of methanol productivity for the same consumption of hydrocarbon feed and oxygen, almost doubling it if the $CO_2$ content of the gaseous hydrocarbons is 30% v/v.

The process described and claimed is therefore able to process hydrocarbon flows even with high $CO_2$ content (converting it into methanol) by integrating technological solutions already available, such as reactors for the production of synthesis gas, Water Gas Shift reactors, electrolysis units, reactors for the synthesis of methanol and separation and purification stages.

The process described and claimed is proposed as a technological choice that consumes, reduces or eliminates $CO_2$ in contrast with the solutions currently in use in which $CO_2$ is sequestrated and re-injected into acid gas fields, putting it back into circulation without ever eliminating it.

It has also been shown that even if the used hydrocarbon reagents contain small volumes of $CO_2$, the process described and claimed enables methanol to be produced with much lower greenhouse gas emissions than those occurring in processes in the known art. This result is made possible through the use of short contact time catalytic partial oxidation (SCT-CPO) technology and water electrolysis in process schemes leading to the synthesis of methanol. The process described and claimed also allows the use of both gaseous hydrocarbon sources of biological origin (e.g. biogas) as a feed for the synthesis gas production section, and renewable energy sources for the generation of electricity to supply the electrolysis process, improving the sustainability of the production processes leading to the production of methanol.

Finally, the process described and claimed allows some process simplifications from an engineering point of view since with the introduction of an electrolysis unit allows the $H_2$ and $O_2$ can be produced in a single unit operation and the PSA and ASU units can be replaced.

In particular, we note that air ASU is an energy-intensive process that cannot always be optimally integrated into methanol synthesis. In fact, together with the $O_2$, ASU produces flows of $N_2$, Ar, He and Ne that contribute to its economic viability. However, the output of these gases cannot always be valorized (particularly in oil & gas extraction contexts). The use of electrolyser enables both very high purity $H_2$ and 02 to be produced and does not require the operations related to the valorization of other gases that are co-produced in ASU. The use of $H_2$ produced by electrolysis reduces or completely avoids the need for recycling purging in methanol synthesis and significantly increases the output of methanol per volume of hydrocarbon gas and oxygen consumed.

Further objects and advantages of the present disclosure will be more clear with the following description and the annexed figures, provided purely as examples and not for limiting the process description, instead illustrating preferred embodiments of the present disclosure.

FIG. 1 illustrates a preferred embodiment according to the present disclosure in which (A) is the short contact time partial catalytic oxidation unit fed with an already desulfurised hydrocarbon gas (1), preferably natural gas, a recycling stream from methanol synthesis (2), 99.9% high purity oxygen (3), superheated steam (4); (B) is the Water Gas Shift unit fed with a portion of the produced synthesis gas (5), while the remaining part (6) is mixed with a mixture of hydrogen and carbon dioxide (7) and sent to a two-phase separator (C) in which water is condensed (10), while the separated top product is synthesis gas (8).

The said synthesis gas (8) is mixed with hydrogen (19) obtained by the electrolysis of water (D). The resulting mixture is compressed in (C1) and mixed with recycled gas (13) before being fed to the methanol synthesis unit (E). The synthesis product (12) is separated (F and G) to obtain recycled gas (2), crude methanol (18) and by-products in aqueous solution and in the form of steam (17). A small purge (15) is extracted from the recycled gas (14) and a portion (13) is compressed in (C2) in order to be fed back to the methanol synthesis unit, while a second minor portion (2) is sent back to the synthesis gas production reactor.

Figure 2:
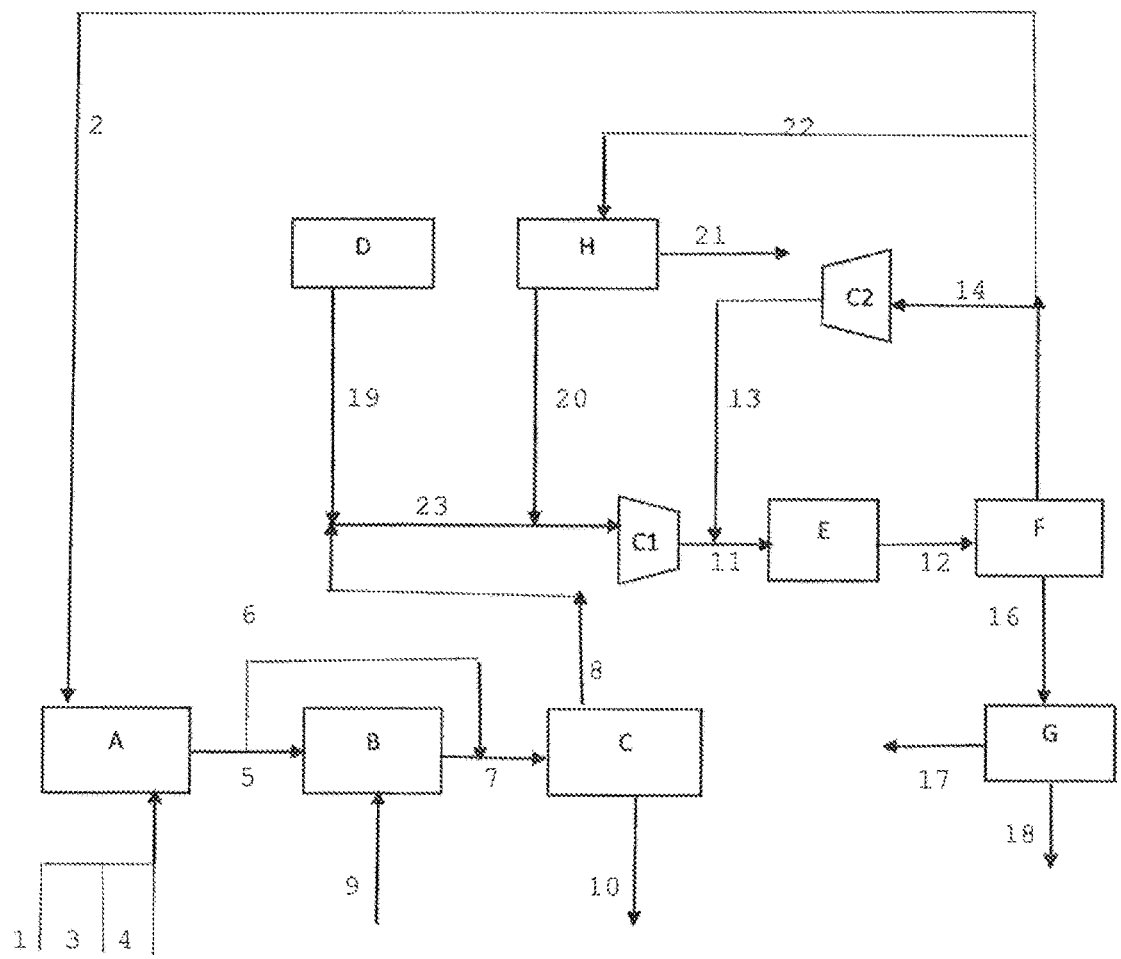
FIG. 2 depicts an embodiment another process for production of methanol according to the present disclosure in which the process depicted in FIG. 1 is modified to include a Pressure Swing Adsorption or PSA unit.

FIG. 2 illustrates a preferred embodiment according to the present disclosure in which the configuration in FIG. 1 is adopted but in addition there is a Pressure Swing Adsorption or PSA unit (H) that separates hydrogen (20) producing off-gases with the emission of $CO_2$ (21). The PSA unit is fed with part of the recycled stream generated in methanol synthesis (22). This scheme can be used mainly in large capacity plants or when for technical and/or economic reasons insufficient electrical energy is available to power the electrolysis processes.

FIG. 3 shows an integrated process for the synthesis of methanol according to the state of the art. FIG. 3 again shows the configuration in FIGS. 1 and 2, where instead of the water electrolysis unit a Pressure Swing Adsorption unit is used, generating off-gases with the emission of carbon dioxide (21).

Figure 4:
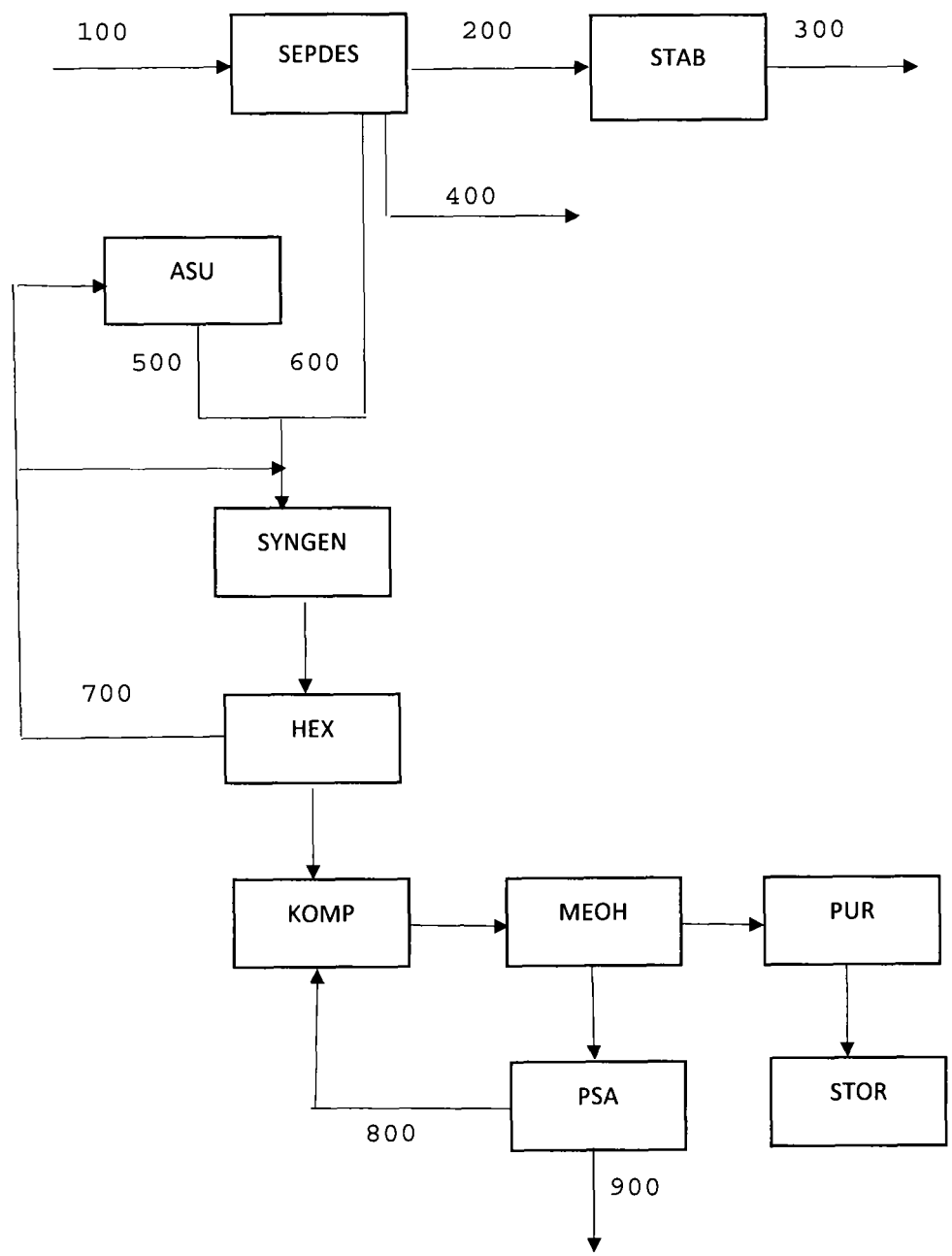
FIG. 4 depicts a process for the production of methanol according to the prior art.

FIG. 4 shows a general diagram of the process units required for the production of methanol according to the known state of the art already previously described in the text.

The process that is the subject of this patent application for the production of methanol from gaseous hydrocarbons, such as natural gas, associated petroleum gas, fuel-gas produced in a refinery or particular chemical plants, or biogas, will now be described in detail, again with reference to FIG. 1 and FIG. 2.

Gaseous hydrocarbons are fed into a desulfurization unit to reduce or eliminate the content of sulfur compounds and thus produce a desulfurized hydrocarbon gas.

The desulfurized gas (1) is mixed with an oxidizing flow (3) chosen from pure oxygen, air or oxygen-enriched air and sent to a catalytic partial oxidation unit where a short contact time catalytic partial oxidation reaction (A) takes place to produce synthesis gas (5). Superheated steam may be added to the desulfurized gas and the oxidizing flow (4). The flows thus obtained can be further pre-heated by making use of the steam obtained by cooling synthesis gas or process flows from other units, using heat exchangers with heat exchange between gases.

The synthesis gas produced can be possibly partly treated in a Water Gas Shift unit (B) fed with a flow of steam (9), thus producing a mixture of hydrogen and carbon dioxide (7). The synthesis gas (5) obtained is cooled and sent to a separator (C) to condense the water (10).

A water electrolysis unit (D) produces hydrogen (19). The produced synthesis gas, without condensed water, is mixed with said hydrogen and compressed (C1).

The mixture of hydrogen and carbon dioxide produced by water gas shift is also cooled and sent to a separator (C) to separate out the condensation water (10). This flow (8) can then be mixed with the hydrogen produced by electrolysis and then compressed (C1). The $H_2$ produced by the electrolysis process is mixed with the synthesis gas (8) to correct the composition of the feed to the methanol synthesis unit to obtain a $(H_2-CO_2)/(CO+CO_2)$ ratio of 2 (v/v).

After compression, the gas mixture is fed to a methanol synthesis unit (E) to produce an effluent (12) which is subsequently separated (F and G) to obtain recycled gas (2), raw methanol (18) and impurities consisting of aqueous condensates and substances dissolved therein (17). The recycled gas may be partly (2) fed to the short contact time catalytic partial oxidation unit, apart from a purge (15) and the remaining portion is compressed (14, C2) and recycled (13) to the methanol synthesis unit.

The synthesis gas is produced in the SCT-CPO reactor at temperatures between 650° C.-1050° C. and then cooled. It is therefore possible to make use of the heat contained in the synthesis gas to produce the steam necessary for pre-heating the reagents by cooling the synthesis gas in heat exchange devices. The synthesis gas can preferably be cooled below 350° C., producing the steam necessary to preheat the reagents and feed the SCT-CPO reactor.

In the process that is the object of the present patent application there may also be a Pressure Swing Adsorption or PSA unit (FIG. 2, H) that separates hydrogen from the input gas at the pressure of the recycling circuit in the methanol synthesis unit (20) with the emission of $CO_2$ at low pressure, typically atmospheric (21). The PSA unit is fed with part of the recycled gas (22) obtained by separating the reaction effluent from the methanol.

The operating conditions under which the short contact time catalytic partial oxidation technology (SCT-CPO) and the methanol synthesis process are able to function are reported in: "Methanol Production via Short Contact Time-Catalytic Partial Oxidation"; Thesis by F. Scirè; Faculty of Civil and Industrial Engineering; Master of Science in Chemical Engineering (A/A 2014/2015).

The SCT-CPO reaction can operate with $O_2/C$ ratios (moles of oxygen/moles of carbon present in the feed, excluding those of $CO_2$) of between 0.15 and 0.70 mole/mole, preferably between 0.45 and 0.65 mole/mole, more preferably between 0.5 and 0.6 mole/mole.

The SCT-CPO reaction can operate with steam/C ratios (moles of water molecules/moles of carbon atoms, excluding those of $CO_2$ present in the feed) between 0.01 mole/mole and 3.5 mole/mole, preferably between 0.5 and 2.5 mole/mole.

In addition, the hydrocarbon feed can contain volumetric percentages of $CO_2$ between 0% and 70%, preferably between 0.5% and 50%, and more preferably between 0.5% and 45% by volume.

The reagents can be fed into SCT-CPO reactors at temperatures between 50° C. and 400° C., preferably between 100° C. and 350° C. The reagents can be fed into SCT-CPO reactors at pressures between 0.0987 atm and 98.7 atm, preferably between 0.493 atm and 59.21 atm, more preferably between 9.87 atm and 39.6 atm.

The short contact time catalytic partial oxidation reaction can preferably take place in a reaction system that includes a short contact time catalytic partial oxidation reactor and a heat exchange system coupled to said reactor and placed downstream of said reactor. The partial catalytic oxidation reactor may have a mixing zone into which the reagents are fed and a truncated cone catalytic zone with an increasing cross-section in which the reactions consuming oxidant take place and the synthesis gas, the reaction effluent, is produced.

The catalytic zone may preferably comprise a multi-layer catalyst bed, each layer of which contains a catalyst comprising a support on which the active part of the catalyst is deposited. The catalytic zone can preferably be contained between two layers of material that act as thermal shields placed upstream and downstream of the catalyst bed. The entire catalytic zone is preferably heated by means of suitable devices for heating the mixture of incoming gases and by the reaction heat.

The catalyst present in each layer of the catalyst bed may include an active part comprising a metal chosen from the group of noble metals, Ni, Co and Fe, and a support chosen from among ceramic oxides with high thermomechanical strength and chemical stability in oxidizing and reducing conditions up to 1500° C.

The noble metals are chosen from Rh, Ru, Pd, Pt, Ir, Au and their mixtures. Rh is the preferred noble metal.

The preferred supports are chosen from Aluminum oxides with alpha, beta and delta phases; Zirconium oxides, also stabilized with Yttrium; Cerium oxides; mixed Magnesium and Aluminum oxides and/or mixed Magnesium or Manganese oxides, more preferably chosen from $MgAl_2O_4$ and $MgMn_{0.25}Al_{1.75}O_4$, hexaluminates, more preferably chosen from $LaAl_{11}O_{19}$ and $LaMnAl_{11}O_{19}$, compounds with a perovskite structure, more preferably chosen from $LaCrO_3$ or $LaCoO_3$, $LaFeO_3$, $LaAlO_3$, $CaTiO_3$, $CaZrO_3$. Alpha-alumina is the preferred ceramic oxide.

The quantity of noble metals present as an active component varies within the range of 0.1%-10% by weight, preferably within the range of 0.2%-5% by weight.

The operating conditions that can be used to conduct methanol synthesis are typically those used in the following processes: a) Haldor-Topsøe; b) Johnson Matthey Catalyst (JM) & Davy Process Technology (DPT); c) Lurgi; d) Toyo Engineering.

The gas fed to the methanol synthesis section must have a composition such as to maintain the value of modulus $M=(H_2-CO_2)/CO+CO_2)$ close to 2 v/v.

All processes for the electrolysis of water may be used in the process covered by this patent application.

Preferably water electrolysis technology may be chosen from 1) alkaline, 2) PEM (Polymer Electrolyte Membrane) and 3) SOEC (Solid Oxide Electrolyzer Cell) technology. Alkaline electrolysis is the most common solution, even though it is still in a further stage of incremental development. PEM technology is newer and less widespread and has high development potential. SOEC technology is not yet commercial. By way of example we point out that commercial alkaline electrolysers are compact and use pressurized $H_2O$ to which KOH is added and from which $H_2$ and $O_2$ are obtained with excellent energy efficiency, even under pressure (20-30 barg). The heart of the process is a series of high efficiency bipolar electrolytic cells that generate $H_2$ and $O_2$. The splitting of water theoretically requires about 3.55 kWh per $Nm^3$ of $H_2$ and is supplied as a direct current flow. However, a fraction of the absorbed power is lost in the form of heat (the energy efficiency declared by the manufacturers is between 60-70%). The $H_2$ and $O_2$ streams are filtered and separated from the moisture that is recycled to the cells.

Excess heat is removed by a water cooling system. Demineralized water is placed in a tank of sufficient volume to allow reasonable operating autonomy and then transferred to the electrolytic system by means of a pump. The three-phase power supply from the grid is converted into direct current by a transformer/inverter system or can be supplied by direct current from, for example, a photovoltaic (PV) or wind power plant. The system is included in a cabinet divided into two chambers separated by a double wall, one enclosing the process unit, the second the power supply section. The resulting flow of $H_2$ is of very high purity (99.9995% v/v) and, in order to obtain it, it is passed through filters that remove the KOH, then into a catalytic reactor to remove the $O_2$ and then into two units to adsorb the water. $O_2$ can also be obtained in very high purity using solutions similar to those used to purify Hz.

Some examples of applications of the present disclosure which are purely descriptive and non-restrictive and which represent preferred embodiments according to the present disclosure will now be described.

EXAMPLES

Comparative Example 1

In the state of the art methanol synthesis follows a scheme similar to that in FIG. 3. Desulfurized natural gas (1), a portion of recycled gas from methanol synthesis (2), superheated steam (4) and a stream of high-purity oxygen (99%) (3) at a pressure of 29.6 atm are preheated using the steam produced by the process itself (not shown in FIG. 3) and mixed at the inlet to the short contact time catalytic partial oxidation reactor (A). The mixture thus composed is converted into synthesis gas (5) by heating to about 850° C.-1050° C. At the reactor outlet the synthesis gas is cooled to below 350° C. in a boiler, producing the steam needed to preheat the reagents and feed the SCT-CPO reactor (not shown in FIG. 3).

The synthesis gas flow from the boiler does not have the optimum composition to feed the downstream section: to adjust some characteristic ratios required by the technology currently in use for methanol synthesis, some of the synthesis gas is sent to a WGS reactor (B) together with a current of steam (9), while the remaining part is not fed to the WGS reactor. The output from the WGS reactor and the synthesis gas directly produced by the catalytic partial oxidation reactor (A) are mixed (7) and cooled in an exchanger to about 45° C., producing more steam. At low temperature the cooled synthesis gas enters a two-phase separator (C), from the bottom of which condensed water is discharged to be sent to water treatment while the anhydrous synthesis gas leaves from the top and is sent to the methanol synthesis section (8).

However, flow (8) still has an M ratio value below the optimal value (2 v/v) and therefore must have a flow of $H_2$ (20) added to it. The necessary $H_2$ is separated by the PSA unit (H), which also generates an off-gases flow (21), a $CO_2$ emission point, said PSA unit being fed partly by the synthesis gas coming from the separator and partly by the recycled gas from methanol synthesis (24): the more $CO_2$ is present in the natural gas feed to the process, the greater will be the amount of synthesis gas that must be sent to the PSA at the expense methanol production.

After the addition of hydrogen, the gas is compressed (C1) to about 79 atm (pressure at which methanol synthesis occurs), and mixed with some of the compressed recycle gas (C2) (13 and 14). After mixing, the resulting flow is fed to the methanol synthesis reactor (E); the output flow from the reactor (12) is cooled to about 50° C., allowing the water and methanol present in it to condense. Finally, using a two-phase separator (F), the recycled gas is separated from the condensates (16) which are depressurized to 5 bar and sent to a final separation stage (G) from which a gaseous flow (17) and raw methanol (18) (consisting of about 85% w/w of methanol and 15% w/w of water) is obtained.

If a natural gas stream with the composition shown in Table 1 is fed to above described process, a material balance is obtained whose main elements are shown in Table 2.

TABLE 1

| Natural gas | % by volume |
|---|---|
| METHANE | 82.15% |
| ETHANE | 9.59% |
| PROPANE | 2.85% |
| ISOBUTANE | 0.64% |
| BUTANE | 0.78% |
| ISOPENTANE | 0.26% |
| PENTANE | 0.22% |
| HEXANE | 0.92% |
| $H_2O$ | 1.01% |
| $CO_2$ | 0.50% |
| HYDROGEN | 0.01% |
| NITROGEN | 1.06% |

TABLE 2

| Methanol synthesis via the production of synthesis gas using SCT-CPO technology | | |
|---|---|---|
| | INPUT | OUTPUT |
| Natural gas [kg/h] | 39948 | — |
| Oxygen [kg/h] | 44395 | — |
| Steam [kg/h] | 26779 | — |
| Off-gases [kg/h] | — | 15438 |
| $CO_2$ [kg/h] | 440 | 7194 in the off-gases and 19788 of $CO_2$ once the all the off-gases are burned |
| Methanol [kg/h] | — | 63765 |

In the table the $CO_2$ output is calculated as two items: that emitted with the off-gases and that obtained by burning all the off-gases.

Some specific indices relating to natural gas and $O_2$ consumption and $CO_2$ emissions per ton of methanol produced are given in Table 3. All species containing C present in off-gases are considered to be oxidized to $CO_2$.

TABLE 3

| SPECIFIC INDICES | |
|---|---|
| $Nm^3_{NG}/ton_{MeOH}$ | 702.66 |
| $Nm^3_{O2}/ton_{MeOH}$ | 487.68 |
| $ton_{CO2\ emitted}/ton_{MeOH}$ | 0.31 |
| $ton_{CO2\ produced}/ton_{MeOH}$ | 0.106 |

Comparative Example 2

A natural gas stream with a high $CO_2$ content shown in Table 4 is fed to the process described in Comparative Example 1 and FIG. 3.

TABLE 4

| Natural gas | % by volume |
|---|---|
| METHANE | 57.84% |
| ETHANE | 6.72% |
| PROPANE | 2.01% |
| ISOBUTANE | 0.55% |
| BUTANE | 0.45% |
| ISOPENTANE | 0.16% |
| PENTANE | 0.18% |
| HEXANE | 0.65% |
| $H_2O$ | 0.71% |
| $CO_2$ | 30% |
| HYDROGEN | 0.73% |

A material balance, whose main elements are shown in Table 5, is obtained, while Table 6 shows the specific indices relating to natural gas and 02 consumption and $CO_2$ emissions per ton of methanol produced. Table 5 shows the $CO_2$ emitted with the off-gases and the $CO_2$ obtained by burning all the off-gases. All species containing carbon present in off-gases are considered to be oxidized to $CO_2$.

TABLE 5

Methanol synthesis via the production of synthesis gas using SCT-CPO technology

| | INPUT | OUTPUT |
|---|---|---|
| Natural gas [kg/h] | 96750 | — |
| Oxygen [kg/h] | 55751 | — |
| Steam [kg/h] | 33629 | — |
| Off-gases [kg/h] | — | 70286 |
| $CO_2$ [Kg/h] | 47121.5 | 29338.5 in off-gases and 93862 once all the off-gases are burned |
| Methanol [kg/h] | — | 63840 |

TABLE 6

SPECIFIC INDICES

| $Nm^3_{NG}/ton_{MeOH}$ | 1253.07 |
|---|---|
| $Nm^3_{O2}/ton_{MeOH}$ | 611.71 |
| $ton_{CO2\ emitted}/ton_{MeOH}$ | 1.47 |
| $ton_{CO2\ consumed}/ton_{MeOH}$ | 0.279 |

Example 1

With reference to FIG. 1 and Comparative Examples 1 and 2, the process comprises two sections: production of synthesis gas through the SCT-CPO process (A) and methanol synthesis (E).

Desulfurised natural gas (1), $O_2$ (3), steam (4) and a flow of recycled gas from methanol synthesis (2) is fed to the SCT-CPO reactor. After being preheated and mixed (not shown in FIG. 1), the feed flows are fed to the reactor where they are converted to produce synthesis gas (5). This is then cooled down to about 350° C. in a boiler, producing steam (not shown in FIG. 1).

As described above, some of the synthesis gas is sent to a WGS reactor (B), while some bypasses it (6): the characteristic $CO/CO_2$ ratio for methanol synthesis is adjusted in this way. The two flows are combined and cooled to about 45° C. before being fed to a separator (C) to remove condensation water (10). The synthesis gas (8) leaves the top of the separator and does not yet have the optimum M ratio for methanol synthesis. As in the previous case, again in this case there is a need to add a flow of $H_2$ (19) to bring the value of M to 2 v/v. In this case $H_2$ is no longer obtained by separating it from the synthesis gas and the recycled gas using PSA, but is obtained from an alkaline electrolyser (D) operating at a pressure of 30-35 atm.

The synthesis gas thus corrected is compressed to about 80 bar (C1), mixed with compressed recycled gas (C2, 13) and then fed to the methanol synthesis reactor (E). The products leaving the reactor are separated and cooled (F, G) to separate a flow of methanol (18) comprising 85% w/w of methanol and 15% w/w of water from the recycled gas (2). A small amount (1% v/v) of all the recycled gas is purged (15) to limit the build-up of inert species in the system.

By feeding a stream of natural gas having the same composition as in Comparative Example 2 (Table 4) with a high $CO_2$ content into the process diagram described above, a material balance is obtained, the main elements of which are shown in Table 7, while natural gas, $O_2$ and $CO_2$ consumption per ton of methanol produced are shown in Table 8. Table 7 shows the $CO_2$ emitted with the off-gases and the $CO_2$ obtained by burning all the off-gases. All species containing C present in off-gasses are considered to be oxidized to $CO_2$.

TABLE 7

Methanol synthesis via the production of synthesis gas using SCT-CPO technology

| | INPUT | OUTPUT |
|---|---|---|
| Natural gas [kg/h] | 96750 | — |
| Oxygen [kg/h] | 58771 | — |
| Steam [kg/h] | 35451 | — |
| Off-gases [kg/h] | — | 8652 |
| Natural gas [kg/h] | — | 7533 |
| $CO_2$ [kg/h] | 47121.5 | 4175 in off-gases and 8686 produced by burning all the off-gases |
| Methanol [kg/h] | — | 124944 |

TABLE 8

SPECIFIC INDICES

| $Nm^3_{NG}/ton_{MeOH}$ | 640.25 |
|---|---|
| $Nm^3_{O2}/ton_{MeOH}$ | 329.48 |
| $ton_{CO2\ emitted}/ton_{MeOH}$ | 0.07 |
| $ton_{CO2\ consumed}/ton_{MeOH}$ | 0.344 |
| $Nm^3_{H2}/ton_{MeOH}$ | 769.89 |

The comparison between Comparative Example 2 and Example 1 shows that the process according to Example 1 enables a production of methanol about twice for the same flow rate and composition of natural gas. In fact, in the former case a significant part (about 50%) of the synthesis gas produced was sent to the PSA unit to produce the hydrogen needed to correct parameter M, while in the process according to Example 1 the hydrogen is supplied by an external source (electrolyser), making it possible to use all of the synthesis gas for methanol synthesis. By eliminating the need to install the PSA unit, the throughputs of off-gases and consequently $CO_2$ emissions are significantly reduced. Table 9 describes the electricity consumption required for electrolysis processes for various methanol production capacities.

TABLE 9

| Case | Natural gas consumed $Nm^3/h$ | $CO_2$ consumed $Nm^3/h$ | $CO_2$ consumed $Nm_3/Day$ | $H_2$ consumed $Nm_3/h$ |
|---|---|---|---|---|
| A | 640 | 175 | 4202 | 770 |
| B | 6403 | 1751 | 42024 | 7699 |

TABLE 9-continued

| Case | | | |
|---|---|---|---|
| C | 9604 | 2626 | 63035 | 11548 |
| D | 19208 | 5253 | 126071 | 23097 |
| E | 40016 | 10944 | 262647 | 48118 |
| F | 80032 | 21887 | 525294 | 96236 |
| G | 133397 | 36482 | 875560 | 160406 |
| H | 152356 | 41667 | 1000000 | 183204 |

| Case | $O_2$ consumed $Nm^3/h$ | Required power MW | Methanol TPh | Methanol TPD |
|---|---|---|---|---|
| A | 329 | 3 | 1 | 24 |
| B | 3295 | 33 | 10 | 240 |
| C | 4942 | 50 | 15 | 360 |
| D | 9885 | 100 | 30 | 720 |
| E | 20593 | 209 | 63 | 1500 |
| F | 41186 | 418 | 125 | 3000 |
| G | 68648 | 697 | 208 | 5000 |
| H | 78405 | 797 | 238 | 5711 |

It should be pointed out that up to cases C and D the electrical power could be entirely produced from renewable sources, while for higher capacities the use of electricity produced from conventional and renewable sources would need to be incorporated.

The invention claimed is:

1. A process for the production of methanol, comprising the following steps:
    a. treating a feed of gaseous hydrocarbons in a desulfurization unit producing a desulfurized hydrocarbon gas, wherein the feed of gaseous hydrocarbons further has a $CO_2$ concentration ranging from 0.5% to 70% by volume;
    b. reacting said desulfurized gas with an oxidising flow by means of a short contact time catalytic partial oxidation reaction to produce synthesis gas;
    c. producing hydrogen by electrolysis of water;
    d. mixing and compressing the synthesis gas and hydrogen; and
    e. sending said compressed mixture to a methanol synthesis unit to produce methanol.

2. The process according to claim 1, wherein some of the synthesis gas produced undergoes a Water Gas Shift reaction to form a flow containing carbon dioxide, carbon monoxide and hydrogen and subsequently said flow is mixed with hydrogen produced by electrolysis.

3. The process according to claim 1, wherein the desulfurized gas is mixed with superheated steam.

4. The process according to claim 1, wherein the desulfurized gas is pre-heated using the steam obtained by cooling the synthesis gas produced in heat exchange devices.

5. The process according to claim 4, wherein the synthesis gas produced is cooled to below 350° C. in a boiler, producing steam.

6. The process according to claim 1, wherein there is also a Pressure Swing Adsorption unit which separates hydrogen from the gas entering the methanol synthesis unit at the pressure of the recycling circuit.

7. The process according to claim 1, wherein the reactants are fed into the short contact time partial catalytic oxidation reactors at temperatures ranging from 50° C. to 400° C.

8. The process according to claim 1, wherein the reactants are fed into the short contact time catalytic partial oxidation reactors at pressures ranging from 0.0987 atm to 98.7 atm.

9. The process according to claim 1, wherein the short contact time catalytic partial oxidation reaction takes place with $O_2/C$ ratios ranging from 0.15 to 0.7.

10. The process according to claim 1, wherein the short contact time catalytic partial oxidation reaction takes place with a steam/C ratio of between 0.01 and 3.5.

11. The process according to claim 1, wherein the methanol synthesis unit includes a reactor for conducting methanol synthesis that operates at temperatures ranging from 250° C. to 350° C. and pressures ranging from 50 to 100 atm.

12. The process according to claim 1, wherein the electrolysis of water is carried out by a technology selected from the group consisting of 1) alkaline, 2) Polymer Electrolyte Membrane and 3) Solid Oxide Electrolyser Cell.

13. The process according to claim 1, wherein the hydrogen mixed and compressed with the synthesis gas is an amount effective to yield a $(H_2-CO_2)/(CO+CO_2)$ ratio of 2 (v/v).

* * * * *